US008480437B2

(12) United States Patent
Dilmaghanian et al.

(10) Patent No.: US 8,480,437 B2
(45) Date of Patent: Jul. 9, 2013

(54) CONNECTOR CARTRIDGE STACK FOR ELECTRICAL TRANSMISSION

(75) Inventors: Farshid Dilmaghanian, Rancho Santa Margarita, CA (US); Hugh Cook, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 0 days.

(21) Appl. No.: 13/493,717

(22) Filed: Jun. 11, 2012

(65) Prior Publication Data
US 2012/0253443 A1    Oct. 4, 2012

Related U.S. Application Data

(62) Division of application No. 12/421,874, filed on Apr. 10, 2009, now Pat. No. 8,215,013.

(60) Provisional application No. 61/044,408, filed on Apr. 11, 2008.

(51) Int. Cl.
*H01R 24/04*    (2006.01)
(52) U.S. Cl.
USPC ............................................................ 439/669
(58) Field of Classification Search
USPC ................ 439/669, 909, 840, 841; 607/37
See application file for complete search history.

(56) References Cited

U.S. PATENT DOCUMENTS

| | | |
|---|---|---|
| 1,934,903 A | 11/1933 | Apple |
| 4,072,154 A | 2/1978 | Anderson et al. |
| 4,105,037 A | 8/1978 | Richter et al. |
| 4,202,592 A | 5/1980 | Rullier et al. |
| 4,262,673 A | 4/1981 | Kinney et al. |
| 4,461,194 A | 7/1984 | Moore |
| 4,934,366 A | 6/1990 | Truex et al. |
| 5,162,686 A | 11/1992 | Royer |
| 5,413,595 A | 5/1995 | Stutz, Jr. |
| 5,817,984 A | 10/1998 | Taylor et al. |
| 5,866,851 A | 2/1999 | Taylor et al. |
| 6,029,089 A | 2/2000 | Hawkins et al. |

(Continued)

FOREIGN PATENT DOCUMENTS

| | | |
|---|---|---|
| WO | WO 97/35636 A1 | 10/1997 |
| WO | 2004/030753 A1 | 4/2004 |
| WO | 20060224208 | 10/2006 |

OTHER PUBLICATIONS

International Search Report completed and mailed Sep. 30, 2009 from corresponding International Application No. PCT/US2009/040184, filed Apr. 10, 2009 (3 pages).

(Continued)

*Primary Examiner* — Phuong Dinh
(74) *Attorney, Agent, or Firm* — Klein, O'Neill & Singh, LLP

(57)    ABSTRACT

Connector assemblies for use with implantable medical devices having easy to assemble contacts are disclosed. The connector assemblies are generally formed by coupling a plurality of ring contacts, sealing rings, and spring contact elements together with at least one holding ring to form a connector having a common bore for receiving a medical lead cable. Contact grooves or spring chambers for positioning the spring contact elements are formed in part by assembling multiple components together. A further aspect is a provision for encasing each connector assembly or stack inside a thermoset layer or a thermoplastic layer before over-molding the same to a sealed housing.

21 Claims, 5 Drawing Sheets

U.S. PATENT DOCUMENTS

| | | | |
|---|---|---|---|
| 6,192,277 B1 | 2/2001 | Lim et al. | |
| 6,428,368 B1 | 8/2002 | Hawkins et al. | |
| 6,498,952 B2 | 12/2002 | Imani et al. | |
| 6,671,554 B2 | 12/2003 | Gibson et al. | |
| 6,878,013 B1 | 4/2005 | Behan | |
| 6,879,857 B2 | 4/2005 | Swanson et al. | |
| 6,887,229 B1 | 5/2005 | Kurth | |
| 6,895,276 B2 * | 5/2005 | Kast et al. | 607/37 |
| 7,003,351 B2 | 2/2006 | Tvaska et al. | |
| 7,047,077 B2 | 5/2006 | Hansen et al. | |
| 7,062,329 B2 | 6/2006 | Ostroff | |
| 7,063,563 B1 | 6/2006 | Hsu | |
| 7,070,455 B2 | 7/2006 | Balsells | |
| 7,083,474 B1 | 8/2006 | Fleck et al. | |
| 7,108,549 B2 | 9/2006 | Lyu et al. | |
| 7,164,954 B2 | 1/2007 | Lefebvre et al. | |
| 7,187,974 B2 | 3/2007 | Haeg et al. | |
| 7,195,523 B2 * | 3/2007 | Naviaux | 439/827 |
| 7,241,180 B1 | 7/2007 | Rentas Torres | |
| 7,263,401 B2 | 8/2007 | Scott et al. | |
| 7,299,095 B1 | 11/2007 | Barlow et al. | |
| 7,303,422 B2 | 12/2007 | Hoffer et al. | |
| 7,326,083 B2 | 2/2008 | Mehdizadeh et al. | |
| 7,429,199 B2 | 9/2008 | Burgess | |
| 2003/0163171 A1 | 8/2003 | Kast | |
| 2007/0239247 A1 | 10/2007 | Camps et al. | |

OTHER PUBLICATIONS

Written Opinion completed and mailed Sep. 30, 2009 from corresponding International Application No. PCT/US2009/040184, filed Apr.10, 2009 (3 pages).

Extended European Search Report dated Aug. 19, 2011 from corresponding European Application No. 09730858.9 (7 pages).

Notice of Allowance mailed May 24, 2012 from related U.S. Appl. No. 12/421,874, filed Apr. 10, 2009.

Office Action mailed Mar. 29, 2012 from related U.S. Appl. No. 12/421,874, filed Apr. 10, 2009.

Final Office Action mailed Jul. 20, 2011 from related U.S. Appl. No. 12/421,874, filed Apr. 10, 2009.

Office Action mailed Feb. 2, 2011 from related U.S. Appl. No. 12/421,874, filed Apr. 10, 2009.

Final Office Action mailed Jul. 22, 2010 from related U.S. Appl. No. 12/421,874, filed Apr. 10, 2009.

Office Action mailed Feb. 26, 2010 from related U.S. Appl. No. 12/421,874, filed Apr. 10, 2009.

Office Action mailed Dec. 15, 2009 from related U.S. Appl. No. 12/421,874, filed Apr. 10, 2009.

Office Action mailed Sep. 2009 from related U.S. Appl. No. 12/421,874, filed Apr. 10, 2009.

* cited by examiner

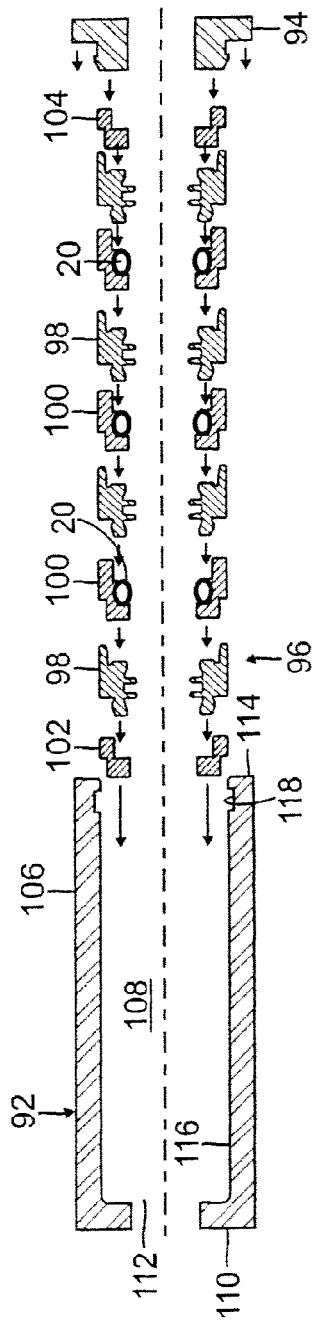
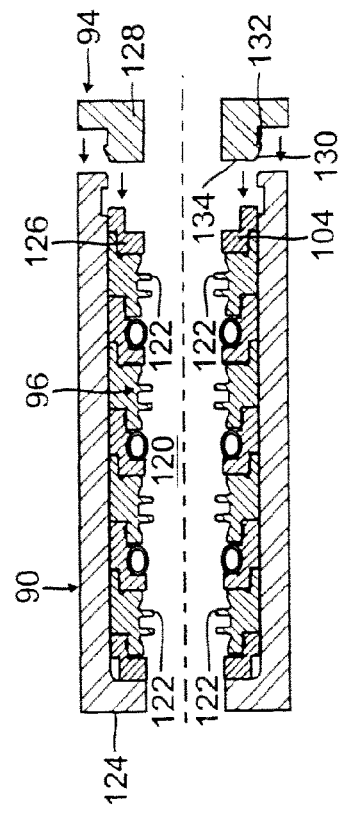
FIG. 4
FIG. 5

CONNECTOR CARTRIDGE STACK FOR ELECTRICAL TRANSMISSION

CROSS-REFERENCE TO RELATED APPLICATIONS

This is a divisional application of application Ser. No. 12/421,874, filed Apr. 10, 2009, now U.S. Pat. No. 8,215,013 which is an ordinary utility application of provisional application Ser. No. 61/044,408, filed Apr. 11, 2008, the contents of each of which are expressly incorporated herein by reference for all purposes.

A connector assembly for electrical transmission between a housing and a pin is generally discussed herein with particular discussions directed to connector assemblies for use with implantable medical devices and connector assemblies having an encapsulated layer made of a dielectric material surrounding a stack of conductive rings and insulative elements.

BACKGROUND

Implantable medical devices for providing electrical stimulation to body tissues, for monitoring physiologic conditions, and for providing alternative treatments to drugs are well known in the art. Exemplary implantable medical devices include implantable cardio defibrillators, pacemakers, and programmable neurostimulator pulse generators, which are collectively herein referred to as "implantable medical devices" or IMDs. These IMDs typically incorporate a hermetically sealed device enclosing a power source and electronic circuitry. Connected to the sealed housing, also known as a "can," is a header assembly. The header assembly includes electrical contact elements that are electrically coupled to the electronic circuits or to the power source located inside the can via conductive terminals. The header assembly provides a means for electrically communicating via an external medical lead cable with the electronic circuits or power source located inside the device to the actual stimulation point.

Industry wide standards have been adopted for, among other things, the dimensions, size, pin spacing, diameter, etc. for the receptacle and the medical lead cable. Furthermore, good electrical contact must be maintained during the life of the implantable medical device, and the medical lead cable for use with the IMD must not disconnect from the receptacle located in the header, yet be detachable for implanting and programming purposes and for replacing the IMD when necessary.

Although prior art connector contacts provide viable options for medical device manufacturers, the overall dimensions of existing receptacles pose manufacturing challenges. Among other things, the challenges of placing stackable rings in between electrically insulating seals, positioning conductive contact elements in between conductive grooves for forming a multi-circuit receptacle, and integrating the contact assembly into the IMD are difficult, costly and time consuming. Accordingly, there is a need for a multi-circuit or multiple contact lead receptacle that not only meets the challenges associated with implantable applications but is also easier to manufacture than a variety of existing receptacles. There is also a need for a receptacle that is easily adaptable with existing implantable medical devices that are easier to manufacture than a variety of existing implantable medical devices.

SUMMARY

Aspects of the present invention include a free standing, axially compressed, connector stack comprising: a plurality of conducting ring elements each having an internal diameter; a plurality of seal elements each comprising an internal diameter; and wherein a conducting ring element is positioned in between two adjacent seal elements; a plurality of canted coil springs each in contact with a corresponding one of the plurality of conducting ring elements; and wherein an encapsulation layer surrounds, at least in part, the stack and two axial ends of the encapsulation layer each overlaps a corresponding one of the plurality of seal elements to maintain the stack axially compressed.

A further aspect of the present invention includes a method for making a free standing axially compressed connector stack comprising a plurality of springs, a plurality of ring contact elements, and a plurality of seal elements having a common bore, tensioning a shaft to axially compress the stack, and applying an encapsulating layer over, at least in part, the stack.

In certain embodiment, the encapsulating layer is made from a dielectric material.

In certain embodiment, the encapsulation layer is a thermoset polymer layer.

Depending on the desired manufacturing needs, the thermoset polymer layer may be applied to the stack by at least one of dipping, spraying, casting, and painting.

In other embodiments, the encapsulation layer is a thermoplastic polymer sleeve. In still others, the encapsulation layer is a machined polymer sleeve with an enclosure cap.

Aspects of the present also include a method for compressing an implantable medical connector stack comprising: using a temporary rod to attach to an end seal and a compression nut or similar device for putting the shaft in tension to axially compress the stack; and maintaining the stack axially compressed after removing the temporary rod from the end seal.

In a yet further aspect of the present invention, a method for assembling a connector comprising: providing an axially compressed stack, said compressed stack comprising an encapsulation layer; placing the compressed stack into a header; and over-molding the header with an implantable thermoplastic or elastomer material to a sealed implantable medical housing.

Other aspects and variations of the connector assemblies summarized above are also contemplated and will be more fully understood when considered with respect to the following disclosure.

BRIEF DESCRIPTION OF THE DRAWINGS

FIGS. 4-6 show an alternative connector stack in different stages of assembly inside an encapsulation layer.

DETAILED DESCRIPTION

The detailed description set forth below in connection with the appended drawings is intended as a description of the presently preferred embodiments of connector assemblies for electrically communicating with pins for medical leads. The connector assemblies provided in accordance with aspects of the present invention are not intended to represent the only forms in which the present invention may be constructed or utilized. The description sets forth the features and the steps for constructing and using the connector assemblies of the present invention in connection with the illustrated embodiments. It is to be understood that the same or equivalent functions and structures may be accomplished by different embodiments and are also intended to be encompassed within the spirit and scope of the present invention, especially those incorporating a combination of features shown in the different embodiments included herein. As denoted elsewhere herein, like element numbers are intended to indicate like or similar elements or features.

Aspects of the present invention comprise the formation of connector stacks, as shown in FIGS. 1-19 of co-pending provisional application No. 61/024,660, filed Jan. 30, 2008, entitled In-Line Connectors, and to application Ser. No. 12/062,895, filed Apr. 4, 2008, entitled CONNECTOR ASSEMBLY FOR USE WITH MEDICAL DEVICES, the contents of each of which are expressly incorporated herein by reference. In one embodiment, the assembled connector assemblies or stacks are each then placed into a mold cavity and over-molded with an implantable grade polymer or elastomer, such as silicone. The individual connector assembly can also be inserted into a pre-molded header, which resembles a housing having a cavity for receiving the connector assembly and one or more openings for placing the connector assembly into the pre-molded header. The one or more openings are then backfilled or sealed, typically after attaching or welding the conductors from the sealed housing to the contact rings, to complete the assembly.

The encased connector may be referred to as a connector header, for placing on a can or sealed housing of an IMD. In one exemplary embodiment, windows (not shown) are left exposed through the over-molded layer adjacent each contact ring. When the header is placed over the can, a plurality of contact conductors in communication with a power source and/or electronic circuits inside the can project upwardly into physical contact with the contact rings. The contact conductors may then welded to a corresponding contact ring to ensure good electrical contact through the windows. The windows are then backfilled and sealed using curable implantable elastomer or polymer.

Figure 1:
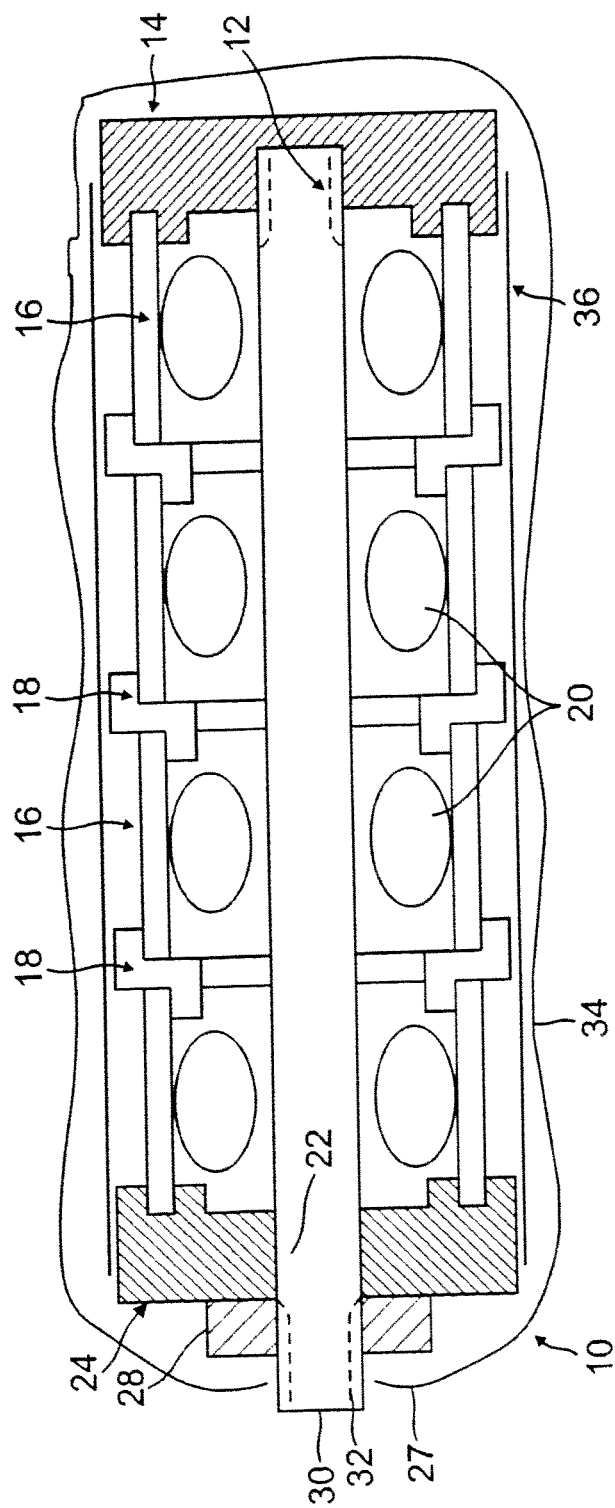
FIG. 1 is a schematic cross-sectional side view of a connector stack usable with an implantable medical housing or device. The stack includes an encapsulation layer of dielectric material surrounding, at least in part, the stack.

In one embodiment, an assembled connector stack is first encapsulated with a thermoset polymer layer or a thermoplastic polymer layer having dielectric properties before it is welded to a plurality of lead conductors and then over-molded in a header to a sealed housing. Referring now to FIG. 1, an assembled connector stack 10 is shown having a removable shaft or installation rod 12 temporarily positioned in the common bore of the stack. The connector stack 10 can embody any of the connector stacks described in the '660 application or the '895 application, and more broadly any connector stack that includes at least one end seal 14, a plurality of conductive elements 16, a plurality of seal elements 18, a plurality of spring contact elements 20 for providing spring forces between a lead cable (not shown but resembles the removable shaft 12) and the plurality of conductive elements, and a common bore 22 that extends between or through the various components. In one embodiment, a second end seal 24 is placed on the end of the stack, at the end opposite the first end seal 14. The second end seal 24 together with the first end seal may be used to compress the alternating stack of conductive elements 16 and seal elements 18, as further discussed below. In a preferred embodiment, the spring contact elements 20 are radial canted coil springs.

In one embodiment, the connector stack 10 is assembled by mounting the various components 14, 16, 18, 20, 24 onto the removable shaft 12 and placing them in mechanical contact with one another as shown in FIG. 1, and as discussed in the '660 application and the '895 application. The number of conductive elements 16, seal elements 18, and spring contact elements 20 used is dependent on the number of electrically conducting nodes or leads a particular application requires, which can vary without deviating from the spirit and scope of the present invention. In the embodiment shown, the stack has four conductive elements 16 and four spring contact elements 20 for use with a four node lead cable (not shown). Again, any number from one to three or greater than four may be practiced without deviating from the spirit and scope of the present invention. Similarly, two or more parallel stacks may be incorporated onto a single can without deviating from the spirit and scope of the present invention.

A set screw (not shown) located on the first end seal 14 is then tightened to secure the first end of the shaft 12 to the end seal 14. A compression nut or similar device 28 is then placed onto the shaft 12, at the shaft's second end 30, and threaded to the threaded section 32 of the shaft to compress the stack 10. In one embodiment, the compression nut 28 is hand tightened. In other embodiments, a set torque amount is used and the nut 28 may be tightened to a designed axial compression by using a marker located on the shaft or by providing a physical stop to delimit further rotation of the nut.

The assembled stack 10 may now be assembled to a header and then attached to a can or sealed electronic housing of an implantable medical device (IMD), such as an implantable pulse generator (IPG). However, in a preferred embodiment the stack 10 is first encapsulated with a thermoset polymer coating before assembly to a header. In one embodiment, the compressed stack 10 is coated with a thin film of sealing material, either by spraying, brushing, or dipping the stack into a thermoset polymer bath and then allowing it to cure, with or without heating. In one embodiment, the thermoset polymer may be epoxy but other implantable grade resins can be used. In other embodiments, the stack is encapsulated with a thermoplastic material, which is thermoformed over the stack, as further discussed below. Thus, aspects of the present invention is understood to include an assembled stack of alternating conductive elements and seal elements that is covered with a thermoset polymer layer; wherein said thermoset polymer layer is configured to maintain the stack of alternating conductive elements and seal elements in a compressed state between two end seals. In a particular embodiment, when axial compression induced by a mechanical means, such as a tension nut, is removed, the thermoset polymer layer is configured to provide an axial compressive force between the two end seals that is greater than compared to an axial compressive force between two end seals without the thermoset polymer layer and without a compression induced mechanical means.

In certain embodiments, a dielectric sleeve 36 is placed over the compressed stack 10 before the same is encapsulated, which is schematically shown in cross-section as two parallel lines. When used, the sleeve 36 is preferably a mesh material, such as non-woven plastic fibers, having pluralities of holes or openings to facilitate bonding and reinforcement of the encapsulated layer 34. As used herein, encapsulation layer or encapsulated layer means a layer that surrounds a connector stack, which comprises a plurality of seal elements, ring contact elements, and spring contact elements, to maintain the stack as a stack unit. The encapsulation layer is understood to differ from a header assembly or unit made from a separate implantable thermoplastic or elastomer material. As further discussed below, the encapsulation layer captures a connector stack and the combination encapsulation layer and connector stack are configured to be placed into a header.

The encapsulated stack 10 may be further processed before installing the same into a header of an IMD by preparing cutouts on the encapsulation 34 for accessing the set screw and the ring contact elements. In one embodiment, a cutout is formed around a set screw (not shown) located on the first end seal 14 to allow access to the set screw for tightening around a pin or rod. In other embodiments, a set screw may be located on the second end seal 24, which will require a corresponding cutout adjustment for accessing the set screw. Additional cutouts are formed one over each of the contact ring elements 16 for welding the ring elements to contact leads 13 (FIG. 2) emanating from the sealed IMD housing, as further discussed below. In another embodiment, a cutout 27 is formed adjacent a compression nut or other similar device 28 for removing or separating the nut from the portion of the encapsulation 34 near the second end seal 24. Once the various cutouts or openings are formed and the set screw backed away from the shaft 12, the shaft can be withdrawn from the common bore 22. In an alternative embodiment, the openings on the encapsulation at the contact ring elements 16 may be made after the shaft is withdrawn from the stack. The openings or cutouts may be made by machining, punching, laser cutting, or waterjet cutting, to name a few.

In compressing the stack 10 before applying an encapsulation layer 34 around it, gaps, slacks, or looseness between the various components are taken up. This process minimizes and possibly eliminates any chances of polymer seeping in between the components during the header encapsulating process and/or during the header over-molding process in which the stack is incorporated into a header with an implantable grade polymer or elastomer. Thus, another aspect of the present invention is the provision for inspecting the stack for penetration of elastomer or polymer materials after the encapsulation process. In one embodiment, inspection is performed by placing the stack under a magnifying glass and looking through the common bore for signs of elastomer and polymer materials.

A method is also herein provided for making a free standing compressed connector stack 10 comprising a plurality of springs 20, ring contact elements 16, and seal elements 18 with an accessible common bore. Free standing is meant to connote not being bounded or confined to a stationary source, such as a stationary clamp. For example, once a stack is assembled, an encapsulated layer is cured over the stack, and a compression nut and assembly rod removed from the stack, the stack is a compressed free standing stack without any compression induced devices. In another embodiment, a method for compressing a stack is provided using a temporary rod attached to an end seal and a compression nut for putting the shaft in tension, which then axially compresses the stack. The compressed stack is capable of remaining compressed once an encapsulated layer is cured thereover and the temporary rod and compression nut removed. In another embodiment, the free standing stack is provided in an assembled compressed state and can simply drop into a header for overmolding to a sealed IMD housing.

In yet another embodiment, an implantable medical stack comprising a common bore is provided in which a conductive ring contact element is axially compressed against two adjacent non-conductive seal elements and the compression is held by an encapsulation layer. A further aspect of the present invention is a method for making an implantable medical stack comprising a common bore in which a conductive ring contact element is axially compressed against two adjacent non-conductive seal elements, the method comprising applying an encapsulation layer around the stack and curing the layer, which can be a thermoset or a thermoplastic polymer, as further discussed below. Another method provided herein comprises the steps of making an implantable medical stack comprising a common bore, a conductive ring contact element axially compressed against two adjacent non-conductive seal elements and the compression is held by an encapsulation layer, wherein a ring groove for retaining a canted coil spring is formed by placing at least one non-conductive seal element adjacent a conductive ring element to create at least one side wall made from a non-conductive material. In yet another embodiment, a method for making an implantable medical stack comprising a common bore in which a non-conductive seal element is axially compressed against two adjacent conductive elements, the method comprising applying an encapsulation layer around the stack and curing the layer, which can be a thermoset or a thermoplastic polymer.

Another method of the present invention is a provision for creating a plurality of retaining bores in a medical connector stack for accommodating a plurality of canted coil springs, each of said bores comprising a conductive bottom wall and at least one side wall made from a non-conducting material, and wherein said stack is held in a compressed state by a cured polymer layer, which can be a thermoset or a thermoplastic polymer, as further discussed below. More broadly, a method is provided for maintaining a stack of assembled components by first placing the stack in compression using a temporary shaft, applying a polymer layer to the stack, curing, hardening, or re-hardening the polymer layer, and removing the temporary shaft to provide an access opening for a common bore.

Figure 2:
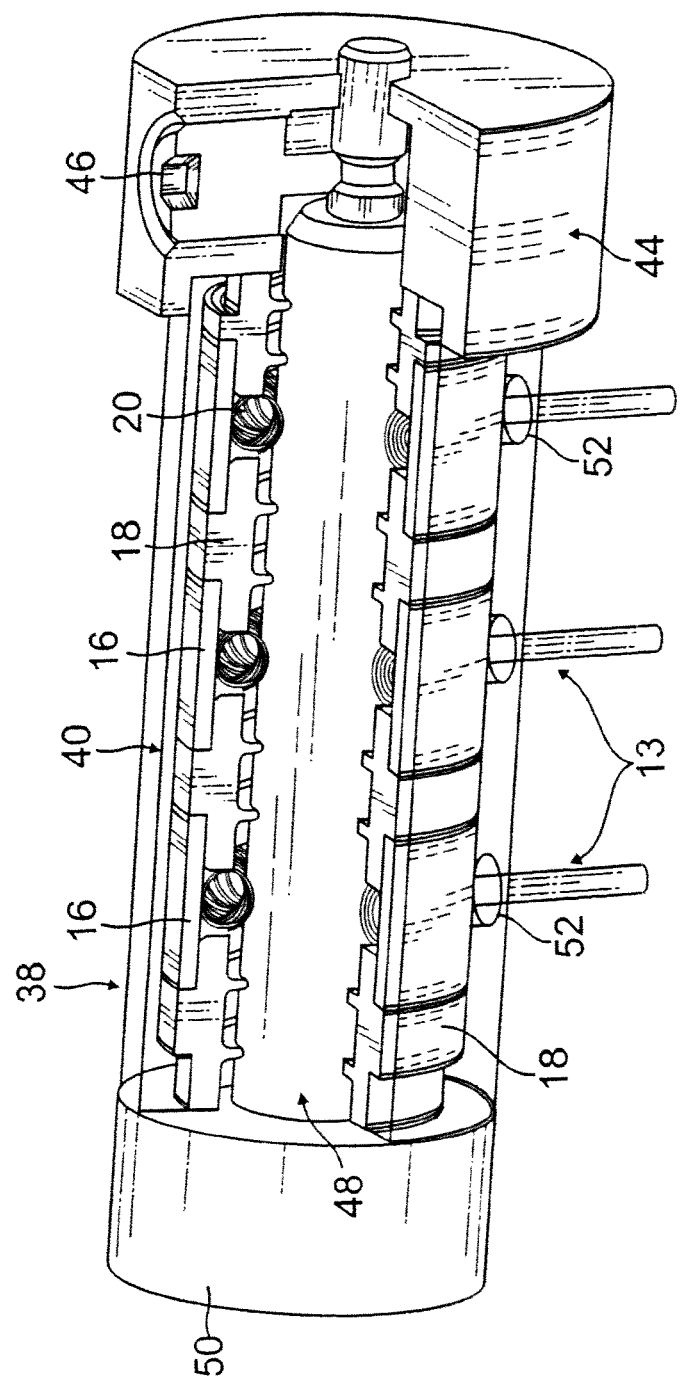
FIG. 2 is a cut-away perspective view of an connector stack usable with an implantable medical housing or device provided in accordance with alternative aspect of the present invention.

Referring now to FIG. 2, a partial perspective cut-away view of an encapsulated implantable medical stack 38 provided in accordance with alternative aspects of the present invention is shown. In the present embodiment, the medical stack 38 can embody any of the stacks disclosed in the '660 application or '895 application, which were previously incorporated by reference. The stack 38 can also have any number of ring contact elements 16, seal elements 18, and canted coil springs 20 depending on the particular application, with only three contact elements 16 and three canted coil springs 20 shown for mating connection with a three-node lead cable.

In the present embodiment, a thermoplastic sleeve 40, which is slightly longer than the length of the stack measured from the two end-most seal elements 18, is placed over part of the stack 38 so that the two ends of the sleeve overhangs the two end-most seal elements 18. The nut 50 is then tightened to a desired compression to axially compress the stack 38, such as by turning the set screw 46 against the groove on the shaft 48. The thermoplastic sleeve 40 may subsequently be heated to near its glass transition temperature and allowed to cool so that the two folded-over ends maintain the stack in the compressed state even after the removable shaft 48 is removed. In a particular embodiment, the thermoplastic sleeve 40 is generally cylindrical in configuration. In another embodiment, after the nut 50 is removed, a second end seal (not shown) is optionally positioned and secured to the stack.

In one embodiment, the sleeve 40 is preferably made from a polysulfone thermoplastic material. However, other thermoplastic polymers may be used, such as heat shrinkable fluro polymer (FEP or PEEK). In one embodiment, the inside diameter of the sleeve is slightly larger than the maximum outside diameter of the stack, excluding the compression plate 44, to provide a slip-on fit when slid over the stack 38. Depending the polymers used to make the sleeve, the thickness of the sleeve can vary. Preferably, it is sufficiently thick to resist axial expansion of the stack after the removable shaft 48 is removed. For polysulfone material, it has been found that a thickness of about 20-30 mils is adequate to maintain the stack in a compressed state. Heat shrinkable materials can also be used to encapsulate the stack. The heat shrinkable material may be slightly longer than the stack so that the heat shrink material folds over the ends of the stack to hold the desized axial compression.

In one embodiment, the sleeve 38 is pre-cut with a plurality of openings. In a particular embodiment, an opening or cutout 52 having a diameter of slightly less than the width of a ring contact element 16 is incorporated and aligned with a corresponding ring contact element. Thus, in the embodiment shown, three openings 52 are provided adjacent three ring contact elements. The openings 52 provide access to the ring contact elements 16 so that that they may be welded to lead wires or conductors emanating from the sealed IMD housing. The stack shown 38, without the removable shaft 48, can then be attached to a header of an IMD. In one embodiment, an additional opening is provided for accessing a set screw used to secure/remove the removable shaft and for later use with a lead cable. Other cutouts and openings may be incorporated as desired.

Thus, aspects of the present invention include methods for forming an encapsulated medical connector stack comprising forming a stack, placing the stack inside a thermoplastic sleeve, and folding two ends of the sleeve over two end axial surfaces of the stack and curing the sleeve. Another feature of the present invention is a method for forming a stack comprising a spring retaining groove comprising a bottom surface defined by a conductive ring element and at least one side wall formed from a non-conducting elastomer, thermoplastic elastomer (TPE), or polymer, and wherein a sleeve comprising a wall surface having a diameter and a length is placed over the stack to form an encapsulation over the stack.

Figure 3:
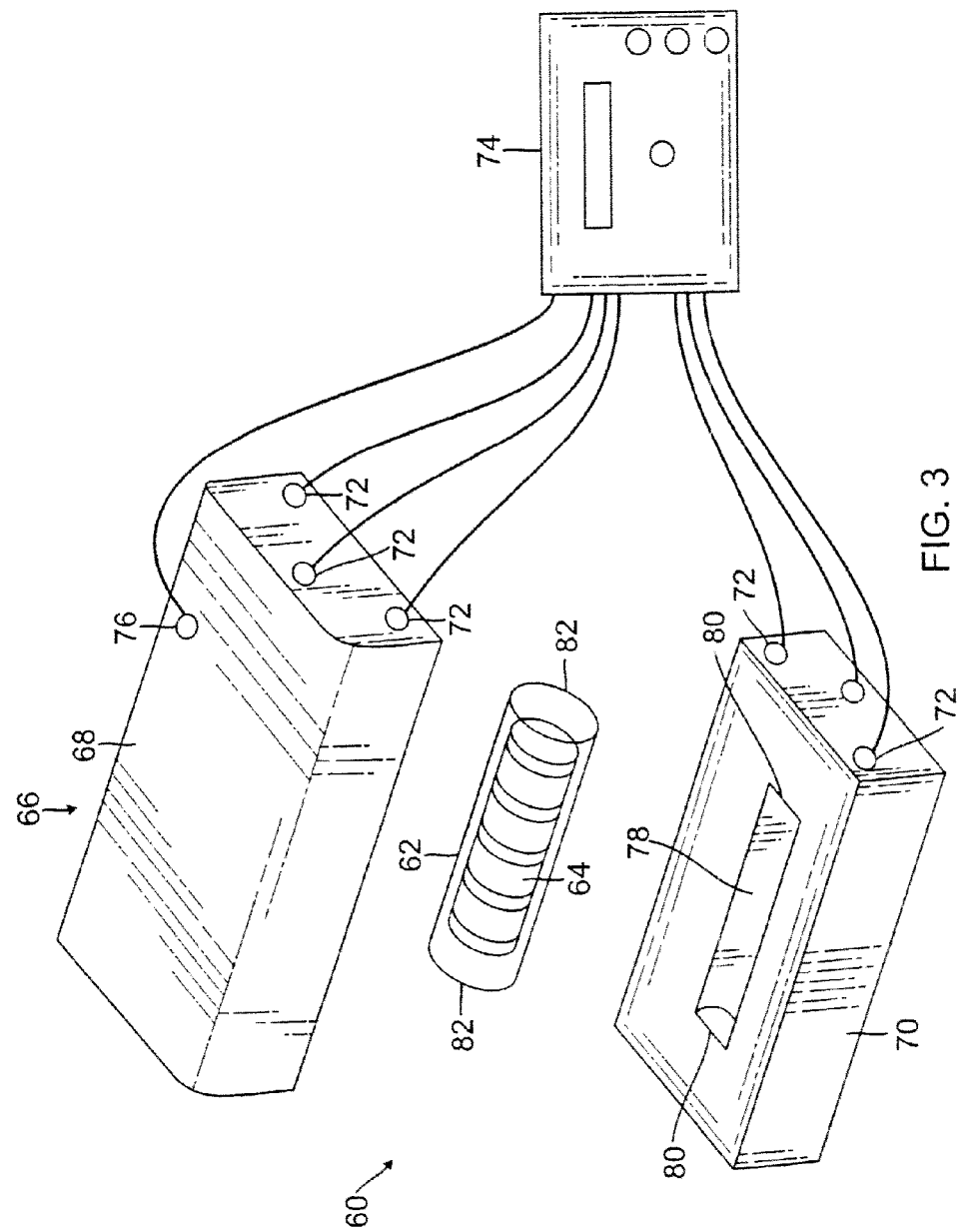
FIG. 3 is a schematic system view of a heated mold system for thermoforming a sleeve over a connector stack.

FIG. 3 is a schematic diagram of a heat forming system 60 for thermoforming a sleeve 62 over a compressed implantable medical connector stack 64 in accordance with aspects of the present invention. In one embodiment, the stack 62 can embody any of the stacks disclosed in the '660 application or '895 application, which were previously incorporated by reference. The stack 64 can also have any number of ring contact elements, seal elements, and canted coil springs depending on the particular application. For purposes of describing the equipment 60 of FIG. 3, the present stack is assumed to be the same as the stack 10 shown in FIG. 1.

In one embodiment, a forming dye 66 comprising an upper housing section 68 and a lower housing section 70 made of a metal material is used. The two housing sections 68, 70 incorporate a plurality of bores 72 for receiving a plurality of electrical resistance heater rods, which are connected to cables that are in turn attached to an induction heater controller 74. One or both housing sections 68, 70 also incorporate a bore 76 for positioning a thermocouple.

Both housing sections 68, 70 incorporate a cavity 78 that together form a tight fitting space for receiving the stack 64. In a particular embodiment, the cavity 78 is sized to form a snug fit around the stack 64. Thus, as the sleeve 62 is slightly longer than the length of the stack, as previously discussed with reference to FIG. 2, the sleeve is forced to fold over by the two ends 80 of the cavity 78 when the combination sleeve and stack is placed in the cavity. When the upper housing section 68 is placed over the lower housing section 70 with the combination sleeve and stack positioned therein, the two ends 80 of the upper cavity 78 also force the sleeve to fold over at its two ends 82. Alignment means may also be incorporated in the heater housing to align the two housing sections when they mate.

The sleeve 62 can now be heated to or near its glass transition temperature and allowed to cool to maintain the stack in a compressed state, as previously discussed. In one embodiment, this is accomplished by energizing the electrical resistance heater rods to heat the upper and lower housing sections 68, 70. Once the two housing sections 68, 70 heat to a set temperature, which is detected by the thermocouple, power to the heater elements is terminated by the controller 74. The sleeve is then allowed to air cool or forced air may be used to circulate air over the two housing sections to more quickly quench the sleeve. Once cooled, the stack with the thermoformed encapsulation may be removed and assembled to a header and to an IMD housing. The addition of the encapsulation layer minimizes and possibly eliminates any chances of polymer seeping in between the components of the stack during the encapsulating process and/or during the overmolding process in which the stack is attached to a header with an implantable grade polymer or elastomer.

Thus, aspects of the present invention include a method for thermoforming a thermoplastic sleeve over an axially compressed implantable medical connector stack having an open common bore by using a heated mold to heat the sleeve to maintain the stack in a compressed state once the sleeve cures. A further method comprises forming an encapsulation around an axially compressed medical connector stack wherein the stack comprises a groove defined by a conducting internal shoulder and at least one side wall comprising an elastomer or a TPE material for retaining a canted coil spring.

A yet further method in accordance with aspects of the present invention is a method for forming a stack over a removable shaft, tensioning the shaft to axially compress the stack, placing the stack inside a thermoplastic sleeve, and placing the combination sleeve and stack into a cavity of a heated mold. In still yet another aspect of the present invention, a method is provided for preventing polymer or elastomer seepage in between a seam of a pair of conductive ring element and seal element of a connector stack, said method comprising the step of curing a sleeve over the connector stack, placing the connector stack and cured sleeve into a header, and back filling the header with curable polymer or elastomer.

FIG. 4 is an exploded cross-sectional side view yet another free standing stack provided in accordance with another aspect of the present invention, which is generally designated 90. In the embodiment shown, the free standing stack 90 comprises an enclosure or housing 92, closure cap 94 and a connector stack 96, which comprises a plurality of seal elements 98, conductive elements 100, spring contact elements 20, and one or more end seals 102, 104. Although shown as an over-under type seal element for forming seals between adjacent ring contact elements for an assembled stack 96 as described in the '895 application, the stack 96 shown is exemplary only and may embody any of the stacks described elsewhere herein or in the '895 application. Also, the number of ring contact elements and spring contact elements may vary depending on the particular application. In the embodiment shown, there are three ring contact elements for a three node application with fewer or more elements contemplated.

In one embodiment, the housing 92 embodies an elongated tube having a wall surface 106 that defines an interior cavity 108. The elongated tube may be generally cylindrical but more preferably is of the size and shape sufficient to accommodate a connector stack 96. The housing has a first end 110 having a through opening 112 and a second end 114, which functions as an inlet for stacking the stack into the interior cavity of the housing. The through opening 112 is configured to accommodate a lead cable, such as a male pin carrying electrode leads, should the lead cable project therethrough. In other embodiments, the first end 110 has a closed end so that an axial end of the lead cable is sealed or confined within the interior cavity 108 of the enclosure. As the housing 92 and enclosure cap 94 are configured to encapsulate the connector stack 96, it may be referred to as an encapsulation layer.

In one embodiment, the enclosure 92 is a machined polymer sleeve comprising an interior wall surface 116 having a machined groove 118 located closer to the second end 114 of the housing than the first end 110. Exemplary polymer materials include peek, polysulfon, polyethylene and silicone. As shown, the interior wall surface is generally square and defines a generally cylindrical interior cavity. The stack may be inserted into the interior cavity one at a time in the order shown or inserted all at once as an assembled stack. In other embodiments, the interior wall surface 116 has a draft angle or a taper that increases from the first end 110 towards the second end 114 such that the inside diameter of the cavity at the second end is larger than the inside diameter of the cavity at the first end. The seal elements 98 are formed with outside diameters that form an interference fit with the inside surface 116 of the housing 92. For a tapered inside housing bore 108, assembly of the stack is facilitated as insertion of the inner most components, i.e., components closest to the first end 110, is easier with a larger inlet provided by the tapered interior wall surface. However, the common bore 120 of the various seal elements should have a constant inside dimension, such as a constant inside diameter defined by the interior seal lips 122 to seal against a lead cable, such as a medical lead cable for medical implants. In one embodiment, the enclosure has a wall thickness of about 25 to about 60 mils depending on the materials used. However, the thickness can vary provided it is sufficiently thick to serve as an enclosure for a free standing stack.

With reference now to FIG. 5 in addition to FIG. 4, the stack 96 is placed inside the interior cavity 108 of the enclosure 92 by first pushing the end seal 102 into the cavity then follow by a seal element 98, and a combination ring contact element 100 and spring contact element 20 and so forth. The spring contact element 20 is preferably placed into physical contact inside the ring contact element 100 and is retained inside the groove provided by the ring contact element prior to placing the combination into the interior cavity of the enclosure 92. In other embodiments, the two are sequentially or serially placed inside the enclosure one at a time. Thus, the present invention is understood to include an enclosure 92 having a wall surface 106 and an end wall 124 for accommodating a connector stack 96. A further aspect of the present invention is an enclosure cap 94 for capping an end of the enclosure housing 92 after the connector stack 96 is placed therein to form a free standing stack 90. The present invention is further understood to include an implantable medical device (IMD), such as an implantable pulse generator, a neurological stimulator, a pacemaker, an implantable cardioverter defibrillator, a cardiac resynchronization therapy device, a spinal cord stimulator, a deep brain stimulator, a vargus nerve stimulator, an interstim neuromodulator, and a cochlear implant device, in which a header having a cavity is sized to accommodate a free standing stack 90. Thus, the IMD is understood to include a first enclosure for enclosing a connector stack and a second enclosure for enclosing the combination first enclosure and connector stack. The second enclosure can be a pre-formed header having a cavity and an opening leading into the cavity and aligned with the common bore of the connector stack.

Figure 6:
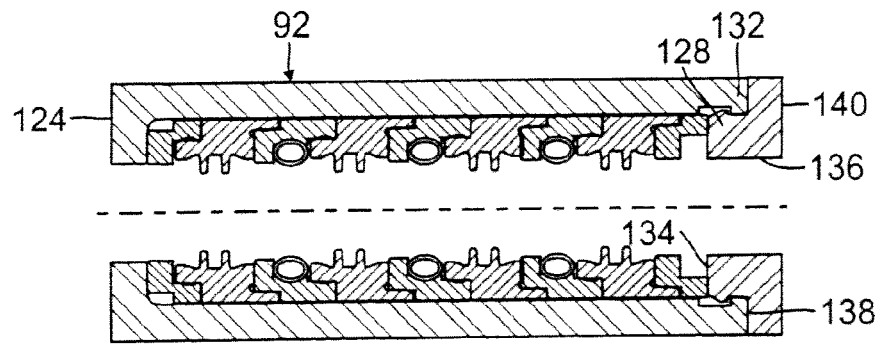

With reference now to FIG. 6 in addition to FIG. 5, the last component to be inserted into the enclosure 92 is an end seal 104. In one embodiment, the end seal 104 has a section, such as an end wall 126, that straddles or overlaps with the machined groove 118. The end wall 126 is configured to be pushed or abutted by a push end 128 on the enclosure cap 94 in the axial direction, which coincides with the lengthwise direction of the connector stack and/or of the enclosure housing 92. In one embodiment, the push end 128 comprises a tapered tip 130 for facilitating insertion of the cap into the opening of the second end 114 of the housing 92. The push end 128 also incorporates a lip 132 for snap-fit engagement with the machined groove 118. The snap-fit engagement seals the seam 138 that delineates the enclosure housing 92 and the enclosure cap 94. In the embodiment shown, the gap or distance between the lip 132 and the axial end surface 134 of the push end 128 may be controlled to provide a desired axial compression on the end seal 104 and hence on the stack 96. In one embodiment, sufficient axial compression is provided so that the first seal element 98 is axially compressed against the first end seal 102. In an alternative embodiment, the enclosure cap 94 is secured to the housing 92 by an external device, such as a clamp, external detents, welding, and bonding. In all embodiments, the combination housing and enclosure cap is understood to include an encapsulation layer comprising a seam.

In the assembled state shown in FIG. 6, the through bore 136 on the enclosure cap 94 aligns with the common bore 120 of the connector stack 96, which may or may not align with the through opening 112 at the first end 110 of the enclosure as it depends on whether an opening is incorporated or not at the first end 110. Thus, an aspect of the present invention is understood to include a housing comprising an end wall for retaining a first end of a connector stack and a cap 94 comprising a push end 128 and/or an end wall 140 for retaining a second end of the connector stack to retain the stack within a cavity defined by the combination enclosure housing and cap. In a still further aspect of the present invention, a connector assembly is provided comprising and encapsulation layer comprising a seam, said encapsulation layer defining an interior cavity and having a connector stack comprising a plurality of seal elements, spring contact elements, and conductive elements. The connector stack preferably further includes at least one end cap located adjacent a seal element. Still more preferably, the end cap comprises a set screw.

Figure 7:
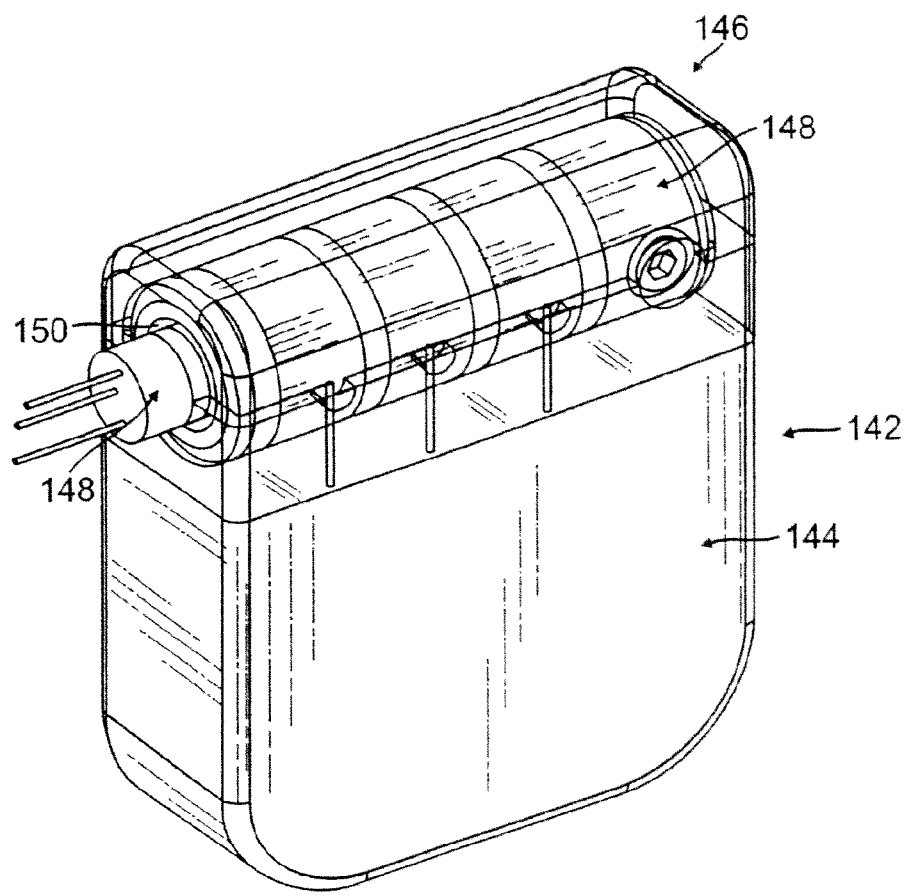
FIG. 7 is an exemplary implantable medical connector incorporating a connector stack in accordance with aspects of the present invention.

With reference now to FIG. 7, an exemplary IMD 142 is shown, which in one particular embodiment is an implantable pulse generator (IPG) but could be any implantable medical devices described above. The IMD 142 comprises a sealed can 144 and a header 146 having a free standing connector stack 148 disposed therein. The free standing connector stack 148 could be any one of the stack described with reference to FIGS. 1-6 above, which may also include any connector stack type described in the '660 application or the '895 application. A medical lead cable 148, only partially shown, is inserted into the common bore of the connector stack, through the header opening 150.

Although limited preferred embodiments and methods for making and using connector assemblies provided in accordance with aspects of the present invention have been specifically described and illustrated, many modifications and variations will be apparent to those skilled in the art. For example, various material changes may be used, incorporating different mechanical engagement means to attach the various components to one another, making use of two or more different materials or composites, making a sealing ring from multiple pieces rather than a singularly molded piece, etc. Moreover, the connector assemblies provided herein may be used in conjunction with an Extension, which is used for testing implanted electrode terminals or implanted activator units so that programs or controls used to manipulate the implanted electrode terminals and the like can be programmed for the IMD. Still alternatively, the connector assembly may be used for any device that requires an in-line connection in which multiple conductive sources are to be relayed between a source generator and a source receiver, whether that device is configured for implanting or otherwise. Still furthermore, although thermoset and thermoplastic polymers are described for encapsulating a stack, other means may be used, such as a mechanical clamp. Accordingly, it is to be understood that the connector assemblies constructed according to principles of this invention may be embodied in other than as specifically described herein. The invention is also defined in the following claims.

What is claimed is:

1. A free standing in-line connector comprising:
    a stack having two axial ends, said stack comprising:
        at least two conductive ring elements each having an internal diameter;
        a plurality of seal elements each comprising an internal diameter; and wherein a conductive ring element is positioned in between two adjacent seal elements;
        at least two canted coil springs each in contact with one of the at least two conductive ring elements; and
    wherein an encapsulation layer surrounds the stack and overlaps at least one of the two axial ends of the stack to maintain the stack axially compressed outside of an implantable medical header.

2. The free standing in-line connector of claim 1, wherein the encapsulation layer is made from a dielectric material.

3. The free standing in-line connector of claim 1, wherein the encapsulation layer comprises a seam.

4. The free standing in-line connector of claim 1, further comprising an end seal located adjacent one of the seal elements.

5. The free standing in-line connector of claim 4, wherein the end seal comprises a threaded bore and a set screw.

6. The free standing in-line connector of claim 1, further comprising a header element attached to a sealed housing of an implantable medical device, wherein the stack and the encapsulation layer are positioned inside the header element.

7. The free standing in-line connector of claim 3, wherein the seam delineates the encapsulation layer into an enclosure cap and an enclosure housing.

8. The free standing in-line connector of claim 1, further comprising a forming dye comprising one or more heating elements and a cavity; and wherein the stack and encapsulation layer are positioned in the cavity.

9. The free standing in-line connector of claim 8, further comprising a thermocouple connected to the forming dye.

10. A free standing, axially compressed, connector stack comprising:
    a plurality of conducting ing elements each having an internal diameter;
    a plurality of seal elements each comprising an internal diameter; and wherein a conducting ring element is positioned in between two adjacent seal elements;
    a plurality of canted coil springs each in contact with a corresponding one of the plurality of conducting ring elements; and
    wherein an encapsulation layer surrounds, at least in part, the stack and two axial ends of the encapsulation layer each overlaps a corresponding end of the stack to maintain the stack axially compressed outside of an implantable medical header.

11. The free standing, axially compressed, connector stack of claim 10, wherein the encapsulation layer is made from a dielectric material.

12. The free standing, axially compressed, connector stack of claim 10, wherein the encapsulation layer comprises a seam.

13. The free standing, axially compressed, connector stack of claim 10, further comprising an end seal located adjacent a seal element.

14. The free standing, axially compressed, connector stack of claim 12, wherein the end seal comprises a threaded bore and a set screw.

15. The free standing, axially compressed, connector stack of claim 10, further comprising a header element attached to a sealed housing of an implantable medical device, wherein said connector stack positioned inside said header element.

16. The free standing implantable, axially compressed, connector stack of claim 11, wherein the seam delineates the encapsulation layer into an enclosure cap and an enclosure housing.

17. A free standing in-line connector comprising:
    a stack having two axial ends, said stack comprising:
        a plurality of conductive ring elements each having an internal diameter:
        a plurality of seal elements each comprising an internal diameter; and wherein at least one conductive ring element is positioned in between two adjacent seal elements;
        a plurality of spring contact elements each in abutting contact with a corresponding conductive ring element;
        the internal diameter of the plurality of conductive ring elements and the internal diameter of the plurality of seal elements defining a common bore:
    wherein an encapsulation layer surrounds the stack and overlaps at least one of the two axial ends of the stack to maintain the stack axially compressed outside of an implantable medical header.

18. The free standing in-line connector of claim 17, further comprising a shaft located in the common bore.

19. The free standing in-line connector of claim 17, further comprising a cap mechanically engaged to an end of the encapsulation layer.

20. The free standing in-line connector of claim 17, further comprising a header element attached to a sealed housing of an implantable medical device, wherein the stack and the encapsulation layer are positioned inside the header element.

21. The free standing in-line connector of claim 17, further comprising a header element attached to a sealed housing of an implantable medical device, wherein the stack and the encapsulation layer are positioned inside the header element.

* * * * *